(12) United States Patent
Yun

(10) Patent No.: US 11,480,562 B2
(45) Date of Patent: Oct. 25, 2022

(54) METHODS OF IDENTIFYING XENOHORMETIC PHENOTYPES AND AGENTS

(71) Applicant: Palo Alto Investors, Palo Alto, CA (US)

(72) Inventor: Anthony Joonkyoo Yun, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 579 days.

(21) Appl. No.: 15/953,287

(22) Filed: Apr. 13, 2018

(65) Prior Publication Data

US 2018/0231527 A1   Aug. 16, 2018

Related U.S. Application Data

(60) Division of application No. 15/062,933, filed on Mar. 7, 2016, now Pat. No. 9,964,536, which is a division of application No. 14/218,163, filed on Mar. 18, 2014, now Pat. No. 9,291,615, which is a continuation of application No. 11/858,819, filed on Sep. 20, 2007, now Pat. No. 8,722,016.

(60) Provisional application No. 60/847,349, filed on Sep. 25, 2006.

(51) Int. Cl.
| | |
|---|---|
| *A61K 49/00* | (2006.01) |
| *G01N 33/00* | (2006.01) |
| *G01N 33/50* | (2006.01) |
| *A01K 45/00* | (2006.01) |
| *C12P 21/00* | (2006.01) |
| *C12Q 1/02* | (2006.01) |

(52) U.S. Cl.
CPC .......... *G01N 33/5085* (2013.01); *A01K 45/00* (2013.01); *A61K 49/0004* (2013.01); *A61K 49/0008* (2013.01); *A61K 49/0021* (2013.01); *C12P 21/00* (2013.01); *C12Q 1/025* (2013.01); *G01N 33/5026* (2013.01)

(58) Field of Classification Search
None
See application file for complete search history.

(56) References Cited

U.S. PATENT DOCUMENTS

| | | | |
|---|---|---|---|
| 8,722,016 B2 | 5/2014 | Yun | |
| 9,291,615 B2 | 3/2016 | Yun | |
| 2003/0092199 A1 | 5/2003 | Hajizadeh | |
| 2003/0162221 A1* | 8/2003 | Bader | C12Q 1/42 435/7.1 |
| 2004/0022924 A1 | 2/2004 | Remacle et al. | |
| 2010/0242139 A1 | 9/2010 | Sinclair | |

FOREIGN PATENT DOCUMENTS

| | | | | |
|---|---|---|---|---|
| WO | WO-2005002672 A2 * | 1/2005 | | C12N 9/16 |

OTHER PUBLICATIONS

Castro et al., Plant Defense and Antimicrobial Peptides. Protein & Peptide Letters, 2005, 12:11-16. (Year: 2005).*
Dixon, RA. Natural products and plant disease resistance. Nature. Jun. 14, 2001;411(6839):843-7. (Year: 2001).*
Brown et al., Bovine spongiform encephalopathy and variant Creutzfeldt-Jakob disease: background, evolution, and current concerns, Emerging Infectious Disease, (Jan.-Feb. 2001); 7(1):6-16.
Gonzalez et al., Differential feeding by marine flagellates on growing versus starving, and on motile versus nonmotile, bacterial prey, Marine Ecology Progress Series, (Dec. 1993) 102:257-267.
Hamel et al., Genomic assessment of follicular marker genes as pregnancy predictors for human IVF, Molecular Human Reproduction, (Feb. 2010) 16(2):87-96.
Hertog et al., Dietary antioxidant flavonoids and risk of coronary heart disease: the Zutphen Elderly Study, Lancet (Oct. 1993) 342(8878):1007-1011.
Jonassen et al., A dietary source of coenzyme Q is essential for growth of long-lived Caenorhabditis elegans clk-1 mutants, PNAS, (Jan. 2001) 98(2):421-426.
Kahn-Kirby et al., Specific Polyunsaturated Fatty Acids Drive TRPV-Dependent Sensory Signaling in Vivo Cell, (Dec. 2004) 119:889-900.
Kitajka et al., Effects of dietary omega-3 polyunsaturated fatty acids on brain gene expression, PNAS, (Jul. 2004) 101(30):10931-10936.
Lamming et al., Small molecules that regulate lifespan: evidence for xenohormesis Molecular Microbiology, (Aug. 2004) 53(4):1003-1009.
Pandey et al., Proteomics to study genes and genomes, Nature, (Jun. 15, 2000) 405(6788):837-846.
Yun et al., Are we eating more than we think? Illegitimate signaling and xenohormesis as participants in the pathogenesis of obesity, Med Hypotheses (Jan. 2006) 67(1):36-40. Epub Jan. 6, 2006.

(Continued)

*Primary Examiner* — Arthur S Leonard
(74) *Attorney, Agent, or Firm* — Peter W. Schroen; Bret E. Field; Bozicevic, Field & Francis LLP

(57) ABSTRACT

Methods of identifying a xenohormetic induced phenotype in an organism are provided. Also provided are methods if using organisms having a known xenohormetically induced phenotype in a number of different applications, such as the identification of xenohormetic agents and the generation of chemical entities and foodstuffs under specific conditions of production governed by xenohormetic effects.

16 Claims, No Drawings

(56) References Cited

OTHER PUBLICATIONS

Ballard et al., Metabolic changes in liver associated with spontaneous ketosis and starvation in cows, Journal of Nutrition 1968 vol. 95 pp. 160-172.
Ecobichon, Chlorinated hydrocarbon insecticides: recent animal data of potential significance for man, Can Med Assoc J. Oct. 10, 1970;103(7):711-6.

* cited by examiner

METHODS OF IDENTIFYING XENOHORMETIC PHENOTYPES AND AGENTS

CROSS-REFERENCE TO RELATED APPLICATIONS

Pursuant to 35 U.S.C. § 119 (e), this application claims priority to the filing date of U.S. Provisional Patent Application Ser. No. 60/847,349 filed Sep. 25, 2006; the disclosure of which application is herein incorporated by reference.

INTRODUCTION

Environmental conditions can have a significant impact on disease conditions in an individual. A given individual's disease condition, e.g., obesity, heart disease, diabetes, etc., can be greatly impacted by the environmental context of the individual. As such, stresses encountered by the individual, both environment and from energy sources, e.g., food, can influence the progression of a given disease condition in the individual. Because of the significant role environment can play in the progression of a disease condition, there is significant interest in the elucidation of how environment cues, e.g., from energy sources, influence disease.

SUMMARY

Methods of identifying a xenohormetically induced phenotype in an organism are provided. Also provided are methods of using organisms having a known xenohormetically induced phenotype in a number of different applications, such as the identification of xenohormetic agents and the generation of chemical entities and foodstuffs under specific conditions of production governed by xenohormetic effects.

DETAILED DESCRIPTION

Methods of identifying a xenohormetic induced phenotype in an organism are provided. Also provided are methods of using organisms having a known xenohormetically induced phenotype in a number of different applications, such as the identification of xenohormetic agents and the generation of chemical entities and foodstuffs under specific conditions of production governed by xenohormetic effects.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, certain methods and materials are now described in greater detail for illustrative purposes.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Aspects of the invention include methods of identifying a xenohormetic induced phenotype in an organism. The term "xenohormesis" as used herein refers to the phenomenon by which a stress signal(s) in a first organism is transmitted to a second organism in a process where the second organism employs the first organism as an energy source. Where xenohormesis occurs, the first organism is stressed in some manner, e.g., by caloric intake, substance intake, and/or environment. This stress may manifest in a number of different phenotypic ways, ranging from outward appearance (e.g., in some way deviating from a normal, wild-type appearance) or in other ways, e.g., by changes in genomic and/or proteomic profiles. Xenohormesis occurs when the second organism that employs the first organism as food (e.g., by eating the first organism) responds in some way to the stress phenotype of the first organism, e.g., by adopting a stressed phenotype itself. As such, xenohormesis can result in a stressed phenotype of a first organism being transmitted to a second organism when the second organism employs the first organism as food. Accordingly, the phrase "xenohormetically induced phenotype" refers to the adoption of a stressed phenotype of a second organism in response to the second organism employing a first stressed organism as food.

The first and second organisms referred to herein may vary considerably, where the term "organism" refers to a live entity that may range in size and complexity from single cell entities to complex multicellular species. As such, organisms of interest include, but are not limited to: single celled organisms, e.g., multicelled organisms, e.g., invertebrates and vertebrates, etc. Accordingly, organisms of interest include, but are not limited to: prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans, and the like.

In the context of the present invention, the first organism serves as an energy source in some manner for the second organism. As such, the second organism views the first organism as a food source and, when placed into proximity of the first organism, may employ the first organism as a food source, e.g., by eating the first organism. As such, in certain embodiments the first organism is the prey of the second organism, such that the first and second organisms have a prey/predator relationship. The first organism may or may not be a natural energy source for the second organism, so long as under appropriate conditions the second organism will employ the first organism as a food source.

In practicing the subject methods, the first step in certain embodiments is to provide a stressed first organism. While the stressed first organism can be obtained from any convenient source, including a commercial source that sells organisms that are known to be stressed in some manner, in certain embodiments this step includes producing the stressed phenotype in the first organism. The stressed phenotype may be produced in the first organism using any convenient protocol, where the protocol employed may include modifying the environment of the first organism in some manner sufficient to produce the stressed phenotype in the first organism. The term "environment" refers broadly to the overall set of conditions in which the first organism is present, including temperature, light, energy source availability, etc. As such, environmental modulation can be accomplished in a variety of different ways, including but not limited to: changing the temperature of the organism, changing the light experienced by the organism, changing the food intake of the organism, administering a stress inducing agent to the organism, etc. In certain embodiments, the stressed first organism is produced by changing the nutritional intake of the first organism e.g., by modifying food intake of the organism, such as by restricting the caloric intake of the organism, by administering a certain kind of stress inducing food to the organism, etc. In certain embodiments, producing a stressed phenotype in the first organism includes confirming that the first organism has obtained the stressed phenotype of interest, e.g., by comparing the organism to a control or reference. As reviewed above, the stressed phenotype that is produced may vary greatly, e.g., from appearance (e.g., skinny) to behavior to certain stressed genomic and/or proteomic profiles.

Upon provision of the first organism having a known stressed phenotype, the first organism is then fed, e.g., by placing the first organism in the vicinity of the second organism, to the second organism. In the subject assay methods, the first organism is brought into contact with one or more of, e.g., a population of, the second organism in a manner such that the second organism can feed on the first organism. In certain embodiments, the first organism is brought into contact with the second organism in a manner such that the second organism can internalize by the first organism. e.g., feed on the first organism. In certain embodiments, internalization will be by ingestion, i.e. orally, such that that the first organism is contacted with the second organism by incorporating the first organism in a nutrient medium, e.g. water, aqueous solution of additional nutrient agents, etc., of the second organisms. As such, in this step of embodiments of the invention, the stressed first organism is fed to the second organism.

Following feeding of the stressed first organism to the second organism, the second organism is evaluated to identify the presence of a xenohormetically induced phenotype. The evaluation may occur immediately after feeding or at some time after feeding, e.g., about 5 minutes or longer after feeding, about 10 minutes or longer after feeding, about 30 minutes or longer after feeding, about 1 hour or longer after feeding, about 6 hours or longer after feeding, about 12 hours or longer after feeding, about 1 day or longer after feeding, about 1 week or longer after feed, etc., depending at least in part on the nature of the first and second organisms. Evaluation may include a single assessment or multiple assessments of the second organism over a given period of time following feeding.

In evaluating the second organism for a xenohormetically induced phenotype, the second organism is assessed for the presence of a stressed phenotype that has been caused by feeding on the stressed first organism. As above, the stressed phenotype for which the second organism is evaluated may be a number of different types of phenotypes, including but not limited to: appearance to behavior to certain stressed genomic and/or proteomic profiles. As such, evaluation of the second organism may include visual assessment of outward phenotypic characteristics, such as visual inspection of the appearance of the second organism, e.g., to determine the presence of stress by identifying the presence of one or more stress correlated appearance characteristics. Evaluation of the second organism may, in certain embodiments, include behavioral assessment of the second organism, e.g., to determine the presence of stress by identifying one or more stress correlated behavioral characteristics. Evaluation of the second organism may, in certain embodiments, include genomic assessment of the second organism, e.g., to determine the presence of stress by identifying one or more stress correlated gene expression characteristics (as may be readily identified by gene expression analysis). Evaluation of the second organism may, in certain embodiments, include proteomic assessment of the second organism, e.g., to determine the presence of stress by identifying one or more stress correlated behavioral characteristics (as may be readily identified using protein expression analysis). In certain embodiments, this evaluation step includes comparison of the second organism to a control or reference organism known not be stressed.

This evaluation step results in the identification of whether the second organism is or is not stressed. Upon comparison to an appropriate control, the presence of the stressed phenotype can be attributed to the second organism employing the first organism as an energy source, e.g., by feeding on the first organism. In these situations, the presence of the stressed phenotype in the second organism can be identified as a xenohormetically induced phenotype. In this manner, the methods of the invention provide a way to identify the presence of a xenohormetically induced phenotype in the second organism.

In certain embodiments, the methods include identifying the first organism as a xenohormetic organism. By "xenohormetic organism" is meant an organism that induces a stress phenotype on a second organism upon being employed by the second organism as an energy source, e.g., upon being eaten by the second organism. As such, xenohormetic organisms are organisms that transmit a stressed phenotype to organisms that employ them in some manner as a source of nutrition.

Embodiments of the invention include methods of screening a candidate compound for xenohormetic activity. By "screening" is meant assessing or evaluating an agent for its ability to modulate (i.e., change) a phenotype in an organism in a xenohormetic fashion. As such, methods include identifying whether an agent enhances or reduces, including inhibits, a xenohormetically induced phenotype in an organism. In practicing these embodiments of the invention, the methods may include contacting a candidate compound with an organism exhibiting a known xenohormetically induced phenotype (such as an organism identified as described above); and evaluating the organism to determine any change in the xenohormetically induced phenotype to identify the compound for xenohormetic activity.

The candidate agent may be contacted with the organism using any convenient protocol, e.g., by placing the agent in the nutrient medium of the organism, by administering the agent to the organism, etc. A large number of different types of compounds may be evaluated for xenohormetic activity. Compounds that may be evaluated encompass numerous chemical classes, though typically they are organic molecules, preferably small organic compounds having a molecular weight of more than 50 and less than about 2,500 daltons. Compounds may include functional groups necessary for structural interaction with proteins, particularly hydrogen bonding, and may include at least an amine, carbonyl, hydroxyl or carboxyl group, such as at least two of the functional chemical groups. The compounds may include cyclical carbon or heterocyclic structures and/or aromatic or polyaromatic structures substituted with one or more of the above functional groups. Compounds of interest are also found among biomolecules including, but not limited to: peptides, saccharides, fatty acids, steroids, purines, pyrimidines, derivatives, structural analogs or combinations thereof.

Compounds of interest may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential agents may also be created using methods such as rational drug design or computer modeling.

Following contact of the compound composition with the organism, the effect of the compound on the organism is determined. The effect of the compound on the organism may be determined by evaluating one or more of a number of different phenotypic parameters. Phenotypic parameters that are evaluated in a given assay of the subject invention may vary widely depending, at least in part, on the nature of the multi-cellular organisms being employed. Phenotypic parameters that may be evaluated in any given assay include one or more of the following: (1) viability; (2) morphological defects; and (3) fecundity. Specific parameters that may be evaluated include one or more of: (1) lethal dose, e.g. LD50, LD10 etc.); (2) growth defects; (3) sterility effect dose; (4) developmental defects; (5) neurologic impairment; (6) life-span modulation, e.g. life span enhancing or shortening; and the like. Of particular interest in certain embodiments is the assessment of whether the organism has reverted to a non-stressed state.

In addition to the above parameters that can be evaluated in the subject methods, the gene expression levels of the test organisms can be assayed, e.g. gene expression levels in treated larva, pupa, and/or flies can be evaluated. The genes can be from "housekeeping" genes that provide basic metabolic information to developmental and tissue specific genes to gauge which tissue or cell type is affected and when. A variety of different gene expression protocols, including arrays based protocols, are known to those of skill in the art, including those described in: EP 0 328 829 B1 and U.S. Pat. Nos. 5,468,613; 5,580,726; 5,599,672; 5,512,462; 5,162,209 and 5,162,209, the disclosures of which are herein incorporated by reference. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299 304; Nguyen et al., Genomics (1995) 29: 207 216; Pietu et al., Genome Res. (1996) 6: 492 503; and Zhao et al., Gene (1995) 166: 207 213.

Patents and patent applications describing methods of genomic expression analysis include, but are not limited to: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992. Also of interest are U.S. Pat. Nos. 6,656,740; 6,613,893; 6,599,693; 6,589, 739; 6,587,579; 6,420,180; 6,387,636; 6,309,875; 6,232, 072; 6,221,653; and 6,180,351.

Also of interest are proteomic analysis assays, e.g., where arrays of polypeptide binding agents are employed. Where the arrays are arrays of polypeptide binding agents, e.g., protein arrays, specific applications of interest include analyte detection/proteomics applications, including those described in U.S. Pat. Nos. 4,591,570; 5,171,695; 5,436, 170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

The effect of the compound on the particular physical parameter or parameters being evaluated may be determined manually or robotically, such that in many embodiments determination of the effect of the compound on the organism is accomplished via an automated procedure.

The effect of the compound on the phenotypic parameter or parameters is then related to the xenohormetic activity of the compound. As such, the effect on the phenotypic parameter(s) is employed to derive a xenohormetic activity assessment for the assayed compound.

Also provided are methods of using organisms having known xenohormetically induced phenotypes to produce a product. By known xenohormetically induced phenotype is meant that the xenohormetic state of the organism is predetermined. As such, in some way the xenohormetically induced condition of the organism has been evaluated and is known. Xenohormetically induced condition may include the presence or absence of a stress phenotype, such that a known xenohormetically induced phenotype can refers organisms that have known stressed phenotype that has been acquired from feeding on another organism and to organisms that are known not to have a stressed phenotype that has been acquired by feeding on another stressed organism.

Producing a product refers broadly to the procedure of using an organism to produce any kind of product, where the product may vary greatly from therapeutic products to nutritional products. As such, methods of the invention include employing organisms known to be not xenohormetic to produce nutritional products, e.g., food. In certain embodiments, the product comprises a protein, e.g., is a meat product, milk, eggs, etc., that is harvested from the organism as food.

In certain embodiments, the organism is known to not have a stressed phenotype because it is an organism that has been administered a sufficient amount of an antixenohormetic agent, e.g., an agent identified using the screening protocols described above.

Aspects of the invention further include methods of identifying a xenohormetic agent. In practicing these embodiments of the invention, the first step may include identifying a first organism that is capable of transmitting a stress phenotype to a second organism, such that the first organism may be viewed as a xenohormetic organism. While such organisms may be identified using any convenient protocol, in certain embodiments this step includes practicing the methods described above to obtain an organism known to be xenohormetic, e.g., that can induce a stressed phenotype on a second organism upon its use as food by the second organism.

Once the xenohormetic organism is identified, the organism is screened to identify the presence of one or more candidate agents to induce xenohormesis. The organism may be screened in this step using any convenient protocol, where the nature of the screen or assay (i.e., testing protocol) will be chosen at least in part on the nature of the candidate agent to be determined. For example, in certain embodiments the candidate agent(s) to be identified is a protein. Proteinaceous candidate agents may be identified in a number of different ways. Identification protocols of interest include, but are not limited to: genomic protocols, proteomic protocols, etc. For example, the gene expression profile of an organism may be evaluated to identify genes that are differentially expressed between xenohormetic and normal organisms, where the differentially expressed nucleic acids may be tested themselves as candidate agents or the protein produces encoded by the differentially expressed nucleic acids may be tested as candidate agents. Any convenient differential gene expression protocol may be employed, where representative protocols of interest include, but are not limited to those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992. Also of interest are U.S. Pat. Nos. 6,656,740; 6,613,893; 6,599,693; 6,589,739; 6,587,579; 6,420,180; 6,387,636; 6,309,875; 6,232,072; 6,221,653; and 6,180,351.

Alternatively, the proteome of the organism may be evaluated to identify candidate agents to induce xenohormesis. Proteomic evaluation protocols of interest include, but are not limited to those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

Following identification of one or more candidate agents, the candidate agents are evaluated for their ability to induce xenohormesis. This step may include contacting one or more candidate agents with a test organism to determine whether the agent can induce a stress phenotype in the test organism. Any convenient protocol for contacting and evaluating may be employed, such as those described above.

The following examples are offered by way of illustration and not by way of limitation.

EXPERIMENTAL

1. Screening for xenohormetic compounds: *E. coli, C. elegans*, and longevity/reproductive sterility.

*Caenorhabditis elegans* N2 variety Bristol is used for screening, and is initially maintained on NGM agar using standard techniques. NGM plates are prepared with the addition of substances to be screened in the presence of 0.1% tergitol (NP-40). *E. coli* strain OP50 is grown on the plates for 2-3 days at room temperature before the addition of embryos or larvae. At various timepoints following initial incubation, sterility is scored by examining animals under a stereo dissecting microscope for the presence or absence of embryos in the uterus. Unless otherwise noted, 100 animals were scored for each fatty acid treatment. After scoring for sterility, the entire population from the plate (200-300 animals) is washed off the plate. To assess viability, SYTO 12 staining of apoptotic corpses is performed. Diamindinophenylindole (DAPI) staining is also performed using the method described, and the DAPI stained samplesare mounted in Vectashield and examined by fluorescence microscopy and Nomarski optics. This method enables identification of particular substances whose effects on inducing stress in the primary diet of *C. elegans, E. coli*, yielded increased/decreased *C. elegans* sterility and longevity and thereby suggests the induction of xenohormesis. Such substances can then be deployed in batch production gene expression systems to yield particular profiles of compounds produced in conjunction with a predefined desired level of stress.

2. Production of xenohormetic foodstuffs: chicken eggs.

Egg laying hens are allocated to groups raised under different ambient conditions (lighting, temperature) and administered different diets for four weeks. Eggs produced during this time are ingested by human subjects—on each day, each subject ingested a particular type of egg. Over the 24 hours following ingestion of each type of egg, cortisol levels and heart rate variability are measured as proxies for level of stress incurred with ingestion, enabling identification of specific conditions or substances that yielded the production of eggs that consistently either promoted or relieved stress.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of identifying a xenohormetic agent, said method comprising:
    a) identifying a first organism selected from the group consisting of an archaea, a bacteria, a member of the kingdom Protista, a fungi and an animal as a xenohormetic organism;
    b) screening the proteome of said first organism for one or more candidate xenohormetic agents; and
    c) contacting said one or more candidate xenohormetic agents with a test organism to determine whether said agent is a xenohormetic agent.

2. The method according to claim 1, wherein said one or more candidate agents are small organic compounds.

3. The method according to claim 1, wherein said one or more candidate agents are peptides.

4. The method according to claim 3, wherein the peptides are proteins.

5. The method according to claim 1, wherein the method further comprises stressing the first organism to produce the one or more candidate xenohormetic agents.

6. The method according to claim 5, wherein the first organism is stressed by modulation of the ambient environmental conditions.

7. The method according to claim 5, wherein the first organism is stressed by modification of nutritional intake.

8. The method according to claim 1, wherein determining whether an agent is a xenohormetic agent comprises visual assessment of the test organism.

9. The method according to claim 1, wherein determining whether an agent is a xenohormetic agent comprises genomic assessment of the test organism.

10. The method according to claim 1, wherein determining whether an agent is a xenohormetic agent comprises proteomic assessment of the test organism.

11. The method according to claim 1, wherein the method further comprises extracting the candidate xenohormetic agent from the first organism.

12. The method according to claim 1, wherein the first organism is an archaea.

13. The method according to claim 1, wherein the first organism is a bacteria.

14. The method according to claim 1, wherein the first organism is a member of the kingdom Protista.

15. The method according to claim 1, wherein the first organism is a fungi.

16. The method according to claim 1, wherein the first organism is an animal.

* * * * *